United States Patent
Yamamoto et al.

(10) Patent No.: US 6,472,573 B1
(45) Date of Patent: Oct. 29, 2002

(54) PROCESS FOR PRODUCING 1,1,1,3,3-PENTAFLUOROPROPANE

(75) Inventors: Akinori Yamamoto; Noriaki Shibata; Tatsuo Nakada; Takashi Shibanuma, all of Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/601,511

(22) PCT Filed: Feb. 5, 1999

(86) PCT No.: PCT/JP99/00537

§ 371 (c)(1),
(2), (4) Date: Aug. 2, 2000

(87) PCT Pub. No.: WO99/48849

PCT Pub. Date: Sep. 30, 1999

(30) Foreign Application Priority Data

Mar. 23, 1998 (JP) ............................................. 10-073626

(51) Int. Cl.$^7$ ............................................... C07C 17/08
(52) U.S. Cl. ........................ 570/164; 570/165; 570/166; 570/167; 570/168; 570/169
(58) Field of Search .................................. 570/164, 165, 570/166, 167, 168, 169

(56) References Cited

U.S. PATENT DOCUMENTS 5,895,825 A * 4/1999 Elsheikh et al. ............ 570/167

* cited by examiner

*Primary Examiner*—Alan Siegel
(74) *Attorney, Agent, or Firm*—Armstrong, Westerman & Hattori, LLP

(57) ABSTRACT

A method of preparation for 1,1,1,3,3-pentafluoropropane (HFC-245fa) wherein the first process gives mainly 1,3,3,3-tetrafluoropropene (1234ze) by reacting 1-chloro-3, 3,3,-trifluoropropene (1233zd) with hydrogen fluoride in the gas phase and subsequently the second process gives 1,1,1,3,3-pentafluoropropane (HFC-245fa) by reacting 1,3,3,3-tetrafluoropropene (1234ze), separated as a component that does not contain hydrogen chloride from crude products obtained by the first process, with hydrogen fluoride in the gas phase. To provide a process that is capable of preparing economically HFC-245fa which does not require the separation of HFC-245fa and 1233zd.

6 Claims, 1 Drawing Sheet

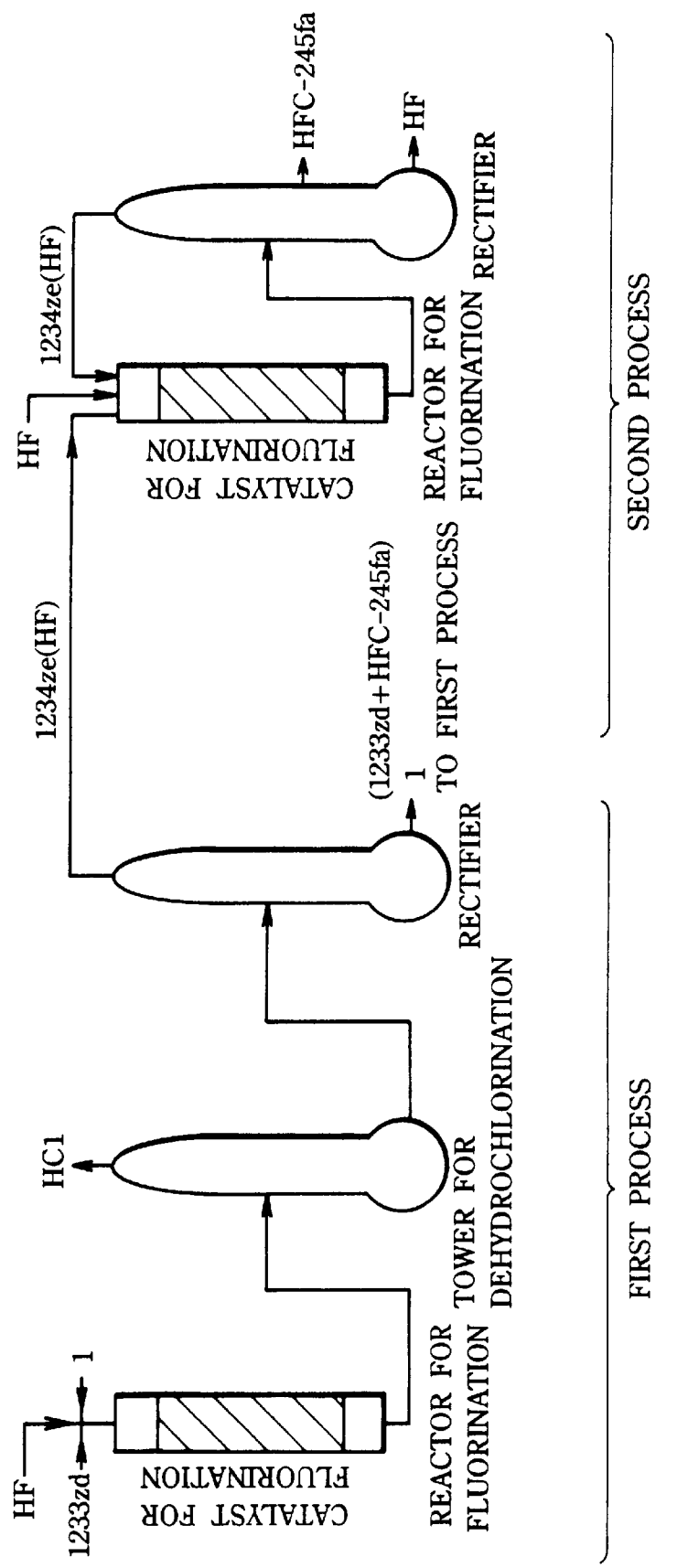

PROCESS FOR PRODUCING 1,1,1,3,3-PENTAFLUOROPROPANE

This application is a 371 of PCT/99/00537 filed Feb. 5, 1999.

INDUSTRIAL FIELDS WHERE THE INVENTION CAN BE UTILIZED

The present invention relates to a preparation method for 1,1,1,3,3-pentafluoropropane (hereinafter, sometimes referred to as HFC-245fa), which is of industrial importance as an HFC blowing agent, a refrigerant, and a jetting agent that does not destroy the ozone layer.

PRIOR ART

Establishment of a preparation method of HFC-245fa has been urgently awaited owing to its excellent performance as described above.

For synthetic methods of preparing HFC-245fa by fluorination in the gas phase, fluorination of 1,1,1,3,3-pentachloropropane (hereinafter, sometimes referred to as 240 fa), fluorination of 1-chloro-3,3,3-trifluoropropene (hereinafter, sometimes referred to as 1233zd) and the like (refer to JP.Patent, 09-183740, A1,1997) are already known.

OBJECT OF THE INVENTION

The present inventors have investigated these preparation methods for HFC-245fa and found the existence of a component that is difficult to separate from HFC-245fa by distillation. The compound that is difficult to separate was carefully isolated followed by identification by NMR. As a result, the compound was identified to be the (E)-1233zd and the boiling point of (E)-1233zd was 20.8° C. (observed value). Because the difference in boiling point between (E)-1233zd and HFC-245fa was 5.3° C. and so extremely small, it was obvious that a large distillation column is required for separation by distillation, and this resulted in initiating a study to solve this problem.

Although the boiling point of (Z)-1233zd which is the other geometrical isomer of 1233zd is not less than 30° C., it is also difficult to separate because it forms an azeotropic composition with HF. The boiling points are given below.

| Boiling Point (observed value) | |
|---|---|
| 245fa | 15.5° C. |
| (E)-1233zd | 20.8° C. |
| (Z)-1233zd | not less than 30° C. |

There exists a separation method by distillation after converting 1233zd contained in HFC-245fa into compounds having a higher boiling point through chlorine treatment (PCT/US 97/05656). However, this method is not preferable, because the 1233zd removed is lost, and a part of the HFC-245fa is also chlorinated and lost.

The object of the present invention is to provide a process for economically preparing HFC-245fa as well as avoiding the requirement for separating HFC-245fa and 1233zd.

CONSTITUTION OF THE INVENTION

Namely, the present invention relates to a preparation method (hereinafter, referred to as the present inventive preparation method) of 1,1,1,3,3-pentafluoropropane (HFC-245fa) comprising: the first process which gives mainly 1,3,3,3-tetrafluoropropene (hereinafter, sometimes referred to as 1234ze) by reacting 1-chloro-3,3,3-trifluoropropene (1233zd) with hydrogen fluoride in the gas phase; and subsequently a second process which gives 1,1,1,3,3-pentafluoropropane (HFC-245fa) by reacting 1,3,3,3-tetrafluoropropene (1234ze), separated as a component that does not contain hydrogen chloride from crude products obtained by the above first process, with hydrogen fluoride in the gas phase.

According to the present inventive preparation method, this can avoid the separation of HFC-245fa and 1233zd which are difficult to separate from each other, avoiding any loss of the product related to chlorination treatment for conventional unavoidable separation.

The present inventors have investigated methods for preparing HFC-245fa in order to solve the above conventional problems and found that equilibriums represented by the following schemes (1) and (2) exists among HFC-245fa, 1234ze and 1233zd in the gas phase reaction.

First Process:

$$CF_3CH=CHCl + HF \rightleftharpoons CF_3CH=CHF + HCl \quad (1)$$
$$(1233zd) \qquad\qquad\qquad (1234ze)$$

Second Process:

$$CF_3CH=CHF + HF \rightleftharpoons CF_3CH_2CF_2H \quad (2)$$
$$(1234ze) \qquad\qquad\qquad (HFC\text{-}245fa)$$

When synthesizing the objective product HFC-245fa, the equilibriums represented by these two schemes indicates that also 1233zd, which is difficult to separate, unavoidably exists if hydrogen chloride (HCl in scheme) exists.

In order to solve this problem, according to the present inventive preparation method, the optimized process of the present invention has been completed by establishing the above second process as a reaction process without hydrogen chloride and compounds generating hydrogen chloride under the reaction conditions, in the final fluorination process for preparing HFC-245fa. Specifically, in the final second process, after purification so that no hydrogen chloride is contained in the reaction material, 1234ze is supplied as a composition without hydrogen chloride and any molecules, which does not contain a chlorine atom in the molecule, leading to a process that does not generate 1233zd. In addition, HFC-245fa and 1234ze are readily separated because the boiling point of 1234ze is −16° C.

According to the present inventive preparation method, 1234ze was adopted as the material for the final reaction process, while if an alternative material, 1,1,3,3-tetrafluoropropene is used, a preparation process for HFC-245fa that does not generate 1233zd as a by-product can be similarly constructed.

Each reaction process will be specifically explained as follows.

First, 1233zd, the starting material submitted to the first process, can be obtained by gas phase fluorination of 1,1,1,3,3-pentachloropropane (240fa). 1233zd may be obtained either as a sole product or as an azeotropic composition with hydrogen fluoride.

This reaction can be carried out using either a fixed bed or a fluid bed.

Further, fluorinating catalysts are not limited; any of them can be used as long as they are capable of fluorinating 240fa to 1233zd. For example, they include: fluorochromium oxide obtained by thermal fluorination of hydrate of chromium hydroxide (III) or chromium trifluoride (III) with hydrogen fluoride; aluminum fluoride, or fluorinated alumina produced by fluorinating alumina with hydrogen fluoride; a supported catalyst in which fluorinated alumina or active charcoal supports at least one element selected from Cr, Zn, Ti, V, Zr, Mo, Ge, Sn, and Pb.

Furthermore, for the reaction conditions, including the reaction temperature, reaction pressure and molar ratio of the starting material to hydrogen fluoride, optimized values can be adopted for each catalyst in consideration of the lifetime of the catalyst, production efficiency, and selectivity of 1233zd.

Also in the fluorination procedures for 240fa by gas phase methods, an arbitrary method can be used. As shown later in the embodiment, this fluorination process is conducted, for example, by the reaction described in Example 1, using 240fa as the material. In this case, although it gives also 1,3-dichloro-3,3-difluoropropene as a product as well as 1233zd, the former compound after separation can be converted to 1233zd by recycling to the reactor followed by refluorination, leading to no loss.

Next, the above first process is a reaction process for preparing 1234ze by fluorination of 1233zd as the starting material, which subsequently is submitted to the above second process. 1233zd which is the starting material for this reaction process may be prepared either by gas phase fluorination of 240fa as described above or by another method. 1234ze may be obtained either as a sole product or as an azeotropic composition with hydrogen fluoride.

The outlet compositions of this fluorination reaction process contain HFC-245fa as well as 1233zd of the starting material and the objective product 1234ze. These are unavoidably generated according to the above equilibrium schemes (1) and (2). HFC-245fa is the final object in the present process; however, purification after taking HFC-245fa from the reaction process is accompanied by the above-mentioned difficulty because separation of HFC-245fa and 1233zd is difficult as described above. In the present inventive preparation method, omitting this separation, the mixture containing HFC-245fa and the unreacted 1233zd can be transferred to the inlet of the first process to be recycled. Namely, 1234ze is separated from the crude products obtained from the first process, and 1233zd and HFC-245fa unseparated from each other are transferred to the first process to be recycled. Consequently, separation of HFC-245fa generated in the first process and 1233zd is not required. Recycled HFC-245fa is converted to 1234ze according to equilibrium scheme (2), leading to no loss in the process.

Further, the distillation process which purifies the outlet compositions of the first process can take only 1234ze as a lower boiling point component in all the organic materials generated, and the other organic materials, 1233zd and HFC-254fa without separation, as higher boiling point components, can be transferred to the inlet of the first process to be recycled. The advantage of the present process is that it enables separation using a smaller distillation column compared to that used to separate 1233zd and HFC-245fa. This reaction can be carried out using either a fixed bed or a fluid bed.

Further, fluorinating catalysts are not limited; any of them can be used as long as they have the capability of fluorinating 1233zd to 1234ze. For example, they include: fluorochromium oxide obtained by thermal fluorination of hydrate of chromium hydroxide (III) or chromium trifluoride (III) with hydrogen fluoride; aluminum fluoride, or fluorinated alumina produced by fluorinating alumina with hydrogen fluoride; a supported catalyst in which fluorinated alumina or active charcoal supports at least one element selected from Cr, Zn, Ti, V, Zr, Mo, Ge, Sn, and Pb.

Furthermore, optimized values can be adopted for the reaction conditions when using each catalyst, including the reaction temperature, reaction pressure and molar ratio of the material to hydrogen fluoride, in consideration of the lifetime of the catalyst, production efficiency, and selectivity of 1234ze.

Also in the fluorination procedures of 1233zd by gas phase methods, arbitrary methods can be used. As shown later in the embodiment, this first process is conducted, for example, by the reaction described in Example 2 using 1233zd as the material. In this case, although 3compounds of 1234ze, 1233zd and HFC-245fa are obtained as the products, a mixture of 1233zd and HFC-245fa without further treatment can be introduced to the reactor to be recycled after separation of the objective product 1234ze by distillation. In this process, it is critical to produce 1234ze as a component containing no hydrogen chloride, while in Example 2, hydrogen chloride is removed by washing with water.

Thus, the absence of any hydrogen chloride in the 1234ze introduced into the second process is a significant requirement so as not to generate 1233zd that is difficult to separate from HFC-245fa, and this is one of the characteristics of the present process.

For the method for removing hydrogen chloride in the 1234ze, an arbitrary method for removing hydrogen chloride in organic materials may be adopted. Typical methods include distillation, washing, membrane separation, and extractive distillation, and these may be combined for removing hydrogen chloride.

Further, the above second process includes a reaction process in which the final objective HFC-245fa is synthesized by fluorination of 1234ze as the starting material. It is no problem that 1234ze as the material is supplied as an azeotropic composition with hydrogen fluoride.

The outlet organic compositions of this reactor for fluorination contain 1234ze and the final objective product HFC-245fa. These compounds can be readily separated by distillation and unreacted 1234ze is preferably introduced to the inlet of the second process to be recycled.

This reaction can be carried out using either a fixed bed or a fluid bed.

Further, fluorinating catalysts are not limited; any of them can be used as long as they have the capability of fluorinating 1234ze to HFC-245fa. For example, they include: fluorochromium oxide obtained by fluorinating a thermally-treated hydrate of chromium hydroxide (III) or chromium trifluoride (III) with hydrogen fluoride; aluminum fluoride, or fluorinated alumina produced by fluorinating alumina with hydrogen fluoride; a supported catalyst in which fluorinated alumina or active charcoal supports at least one element selected from Cr, Zn, Ti, V, Zr, Mo, Ge, Sn, and Pb.

Furthermore, optimized values can be adopted for the reaction conditions when using each catalyst, including the reaction temperature, reaction pressure and molar ratio of the material to hydrogen fluoride, in consideration of the lifetime of the catalyst, production efficiency, and selectivity of HFC-245fa.

Also in the fluorination procedures of 1234ze by gas phase methods, an optional method can be used. As shown later in the embodiment, this second process is conducted by the reaction as described in Example 3 using, for example, 1234ze as the material. In this case, the products include only 1234ze and HFC-245fa which can be readily separated by distillation.

FIG.1 shows an example of a plant that can be used to conduct the present inventive preparation method.

In the present inventive preparation method, 240fa of a material is readily obtained from an addition reaction of carbon tetrachloride with vinyl chloride (refer to Journal of Molecular Catalysis, Vol. 77, 51, 1992 and Journal of the Society of Industrial Chemistry, Vol. 72, No. 7, 156, 1969). Methods of synthesizing 1233zd using 240fa as the material are described in JP.Patent, 09-183740, A1, 1997, JP.Patent, 09-194404, A1, 1997 and U.S. Pat. No. 5,710,352. Further, the known method using tetrachloropropene as the material is described in WO 97-08117.

INDUSTRIAL AVAILABILITY OF THE INVENTION

According to the present inventive preparation method, in the final second process which prepares HFC-245fa significant for industry: 1234ze containing no chlorine atom in the molecule is used as the material; purification is performed so that hydrogen chloride is not contained in the reaction material followed by supplying; and the process is controlled so that 1233zd is not generated. Therefore, the separation of HFC-245fa and 1233zd being difficult to be separated from each other can be avoided, leading to no loss of the materials relating to chlorination treatment for the conventional unavoidable separation. Further, HFC-245fa is readily separated from 1234ze. Herein, 1233zd used as the starting material in the first process is useful as an intermediate for medicines and agricultural chemicals when introducing a trifluoropropyl group.

BRIEF DESCRIPTION OF THE DRAWING

FIG. shows a schematic flowchart for an example of the plant in which the present inventive preparation method may be conducted.

EXAMPLE

Examples of the present invention are illustrated as follows.

Example 1

Preparation of 1-chloro-3,3,3-trifluoropropene:

A catalyst for fluorination was obtained by thermally treating chromium hydroxide precipitated from chromium nitrate solution using aqueous ammonia. The catalyst was fluorinated by independently passing hydrogen fluoride prior to the reaction.

20 g of the above prepared catalyst was charged in a Hastelloy C-type reaction tube, 20 mm in internal diameter and 700 mm in length, and the temperature was elevated to 350° C. in a current of nitrogen. Thereafter, the nitrogen was stopped, and 1,1,1,3,3-pentachloropropane (240fa) and hydrogen fluoride were introduced at 40 cc/min and at 200 cc/min, respectively.

After washing the produced gas with water followed by drying, the gas composition was analyzed by gas chromatography to obtain a mixed gas having the following composition ratio:

| | |
|---|---|
| 1,3,3,3-tetrafluoropropene (1234ze) | 0.3% |
| 1,3-dichloro-3,3-difluoropropene | 1.6% |
| 1-chloro-3,3,3-trifluoropropene (1233zd) | 98.1% |

1-chloro-3,3,3-trifluoropropene was obtained by purifying these.

1-chloro-3,3,3-trifluoropropene obtained as described above at 20 cc/min accompanied by hydrogen fluoride at 200 cc/min was passed into a similar reaction tube to the one above. The temperature was brought to 370° C.

After washing the produced gas with water followed by drying, the composition of gas was analyzed by gas chromatography to obtain a mixed gas having the following composition ratio:

| | |
|---|---|
| 1,3,3,3-tetrafluoropropene | 45.6% |
| 1,1,1,3,3-pentafluoropropane (HFC-245fa) | 2.7% |
| 1-chloro-3,3,3-trifluoropropene | 51.6% |

The gas generated was rectified to give 1,3,3,3-tetrafluoropropene.

1,3,3,3-tetrafluoropropene obtained as described above at 20 cc/min accompanied by hydrogen fluoride at 200 cc/min was passed into a similar reaction tube to the one above. The temperature was brought to 250° C.

After washing the produced gas with water followed by drying, the composition of gas was analyzed by gas chromatography to obtain a mixed gas having the following composition ratio:

| | |
|---|---|
| 1,3,3,3-tetrafluoropropene | 33.7% |
| 1,1,1,3,3-pentafluoropropane | 66.3% |

Thus, 1,1,1,3,3-pentafluoropropane was produced that does not contain 1-chloro-3,3,3-trifluoropropene which is difficult to separate.

Example 2

1-chloro-3,3,3-trifluoropropene obtained by a similar method to Example 1 at 20 cc/min accompanied by hydrogen fluoride at 300 cc/min was passed into a similar reaction tube to the one in Example 1. The temperature was brought to 350° C.

After washing the produced gas with water followed by drying, the composition of gas was analyzed by gas chromatography to obtain a mixed gas having the following composition ratio:

| | |
|---|---|
| 1,3,3,3-tetrafluoropropene | 47.1% |
| 1,1,1,3,3-pentafluoropropane | 7.0% |
| 1-chloro-3,3,3-trifluoropropene | 45.9% |

This gas generated was rectified to give 1,3,3,3-tetrafluoropropene.

1,3,3,3-tetrafluoropropene obtained as described above at 20 cc/min accompanied by hydrogen fluoride at 200 cc/min was passed into a similar reaction tube to the one above. The temperature was brought to 230° C.

After washing the produced gas with water followed by drying, the composition of gas was analyzed by gas chromatography to obtain a mixed gas having the following composition ratio:

| | |
|---|---|
| 1,3,3,3-tetrafluoropropene | 19.7% |
| 1,1,1,3,3-pentafluoropropane | 80.3% |

Thus, even if the reaction temperature was changed, 1,1,1,3,3-pentafluoropropane was produced that does not contain 1-chloro-3,3,3-trifluoropropene which is difficult to separate.

Example 3

1-chloro-3,3,3-trifluoropropene obtained by a similar method to Example 1 at 10 cc/min accompanied by hydrogen fluoride at 150 cc/min was passed into a similar reaction tube to the one in Example 1 into which fluorinated alumina is charged. The temperature was brought to 350° C.

After washing the produced gas with water followed by drying, the composition of gas was analyzed by gas chromatography to obtain a mixed gas having the following composition ratio:

| | |
|---|---|
| 1,3,3,3-tetrafluoropropene | 47.3% |
| 1,1,1,3,3-pentafluoropropane | 6.0% |
| 1-chloro-3,3,3-trifluoropropene | 46.7% |

The gas generated was rectified to give 1,3,3,3-tetrafluoropropene.

1,3,3,3-tetrafluoropropene obtained as described above at 10 cc/min accompanied by hydrogen fluoride at 100 cc/min was passed into a similar reaction tube to the one above. The temperature was brought to 230° C.

After washing the produced gas with water followed by drying, the composition of gas was analyzed by gas chromatography to obtain a mixed gas having the following composition ratio:

| | |
|---|---|
| 1,3,3,3-tetrafluoropropene | 18.8% |
| 1,1,1,3,3-pentafluoropropane | 81.2% |

Thus, even if fluorinated alumina was used as a catalyst, 1,1,1,3,3-pentafluoropropane was produced that does not contain 1-chloro-3,3,3-trifluoropropene which is difficult to separate.

Example 4

The temperature of the first reactor was brought to 370° C. shown in Example 1, and a stainless steel distillation column for dehydrochlorination and stainless steel rectifying equipment were installed at the outlet so as to enable rectification of the generated gas. 1-chloro-3,3,3-trifluoropropene at 20 cc/min and hydrogen fluoride at 200 cc/min were introduced into the first reactor. The products were led to the distillation column and then dehydrochlorinated, and 1,3,3,3-tetrafluoropropene and HF were drawn from the upper stage of the rectifier. From the bottom of the rectifier, unreacted 1-chloro-3,3,3-trifluoropropene, hydrogen fluoride and 1,1,1,3,3-pentafluoropropane as high boiling point substances were transferred to the first reactor to be recycled. As the distillation column was stabilized, the amount of hydrogen fluoride introduced was reduced to stabilize the reaction system.

Part of the outlet gas from the first reactor at this time was sampled followed by washing with water and then analyzed by gas chromatography, and it proved to be a mixed gas having the following composition:

| | |
|---|---|
| 1,3,3,3-tetrafluoropropene | 48.3% |
| 1,1,1,3,3-pentafluoropropane | 2.8% |
| 1-chloro-3,3,3-trifluoropropene | 48.9% |

After drawing the gas from the upper stage of the rectifier followed by washing with water, the sample was analyzed by gas chromatography, which showed a purity of 1,3,3,3-tetrafluoropropene not less than 99.6%; in addition, the gas did not contain 1-chloro-3,3,3-trifluoropropene as a starting material.

Thus, it was proved that 1,3,3,3-tetrafluoropropene was obtained with good purity from 1-chloro-3,3,3-trifluoropropene.

Example 5

The temperature of the second reactor was brought to 230° C. shown in Example 1, and stainless steel rectifying equipment was installed at the outlet so as to enable rectification of the generated gas.

1,3,3,3-tetrafluoropropene at 20 cc/min and hydrogen fluoride at 200 cc/min were introduced into the second reactor. The products were led to the rectifier, 1,3,3,3-tetrafluoropropene was drawn off as organic material from the upper stage of the rectifier and transferred to the second reactor to be recycled. From the center of the rectifier, 1,1,1,3,3-pentafluoropropane which is an organic material was drawn off. From the bottom of the rectifier, excess hydrogen fluoride was drawn off. Both of these were transferred to the second reactor to be recycled. As the distillation column was stabilized, the amount of hydrogen fluoride introduced was reduced to stabilize the reaction system.

Part of the outlet gas of the second reactor at this time was sampled followed by washing with water and then analyzed by gas chromatography, and it proved to be a mixed gas having the following composition:

| | |
|---|---|
| 1,3,3,3-tetrafluoropropene | 17.2% |
| 1,1,1,3,3-pentafluoropropane | 82.8% |

After drawing off the gas from the center stage of the rectifier followed by washing with water, the sample was analyzed by gas chromatography which showed a purity of 1,1,1,3,3-pentafluoropropane not less than 99.8%; in addition, the gas did not contain 1-chloro-3,3,3-trifluoropropene which is difficult to separate.

Thus, it was proved possible to obtain 1,1,1,3,3-pentafluoropropane with good purity from 1,3,3,3-tetrafluoropropene.

Comparative Example 1

The equipment used was similar to that of Example 4, except that an SUS distillation column for dehydrochlorination was not used. SUS rectifying equipment was installed so as to enable rectification of the generated gas.

1-chloro-3,3-trifluoropropene at 20 cc/min and hydrogen fluoride at 200 cc/min were introduced into the first reactor. The products were led to the rectifier and 1,3,3,3- tetrafluoropropene and hydrochloric acid produced were drawn off from the upper stage of the rectifier. 1,1,1,3,3-pentafluoropropane from the center of the rectifier, and excess hydrogen fluoride from the bottom, were transferred to the reactor to be recycled. As the distillation column was stabilized, the amount of hydrogen fluoride introduced was reduced to stabilize the reaction system.

A mixture of this 1,3,3,3-tetrafluoropropene and hydrochloric acid as well as hydrogen fluoride at 200 cc/min were together led to the second reactor to be reacted. The outlet gas of the second reactor at this time was washed with water and then analyzed by gas chromatography, and it proved to be a mixed gas having the following composition:

| | |
|---|---|
| 1,3,3,3-tetrafluoropropene | 15.9% |
| 1,1,1,3,3-pentafluoropropane | 77.2% |
| 1-chloro-3,3,3-trifluoropropene | 6.9% |

Thus, it was clear that 1-chloro-3,3,3-trifluoropropene which is difficult to separate is generated by performing the final process without dehydrochlorination.

What is claimed is:

1. A preparation method for 1,1,1,3,3-pentafluoropropane comprising:

a first process which gives a reaction mixture consisting mainly of 1,3,3,3-tetrafluoropropene by reacting 1-chloro-3,3,3-trifluoropropene with hydrogen fluoride in a gas phase;

a subsequent process of removing HCl and 1-chloro-3,3,3-trifluoropropene substantially completely from the said reaction mixture without removing hydrogen fluoride; and a further subsequent process which gives 1,1,1,3,3-pentafluoropropane by reacting 1,3,3,3-tetrafluoropropene which is obtained by reacting 1,3,3,3-tetrafluoropropene, in an azeotropic mixture with hydrogen fluoride that does not contain HCl and 1-chloro-3,3,3-trifluoropropene, with hydrogen fluoride in a gas phase.

2. A preparation method claimed in claim 1 wherein 1,3,3,3-tetrafluoropropene is separated from crude products obtained by said first process, and 1-chloro-3,3,3-trifluoropropene and 1,1,1,3,3-pentafluoropropane unseparated from each other are transferred to said first process to be recycled.

3. A preparation method claimed in claim 1 or 2 wherein unreacted 1,3,3,3-tetrafluoropropene is separated together with hydrogen fluoride in said second process followed by being transferred to said second process to be recycled.

4. A preparation method claimed in claim 1 or 2 wherein 1,3,3,3-tetrafluoropropene obtained by said first process is prepared as an azeotropic composition with hydrogen fluoride and submitted to the material in said second process.

5. A preparation method claimed in claim 1 or 2 wherein 1-chloro-3,3,3-trifluoropropene which is obtained by reacting 1,1,1,3,3-pentachloropropane with hydrogen fluoride in the gas phase is submitted to the material in said first process.

6. A preparation method claimed in claim 5 wherein said 1-chloro-3,3,3-trifluoropropene which is prepared as an azeotropic composition with hydrogen fluoride is submitted to the material in said first process.

* * * * *